US00PP08923P

United States Patent [19]

Bradford et al.

[11] Patent Number: Plant 8,923

[45] Date of Patent: Oct. 4, 1994

[54] NECTARINE TREE (KAY DIAMOND)

[76] Inventors: Lowell G. Bradford, 12439 E. Savana Rd.; Norman G. Bradford, 11875 E. Savana Rd., both of Le Grand, Calif. 95333

[21] Appl. No.: 183,353

[22] Filed: Jan. 19, 1994

[51] Int. Cl.[5] ..... A01H 5/00
[52] U.S. Cl. ..... Plt./41.3
[58] Field of Search ..... Plt. 41.3

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the third week in June, with first picking on Jun. 16, 1993. The fruit is uniformly large in size, excellent in flavor, attractively globose in shape, freestone in type, very firm in texture, and full red in skin color. The variety was developed as a hybridized seedling from the selected seed parent of May Diamond Nectarine (U.S. Plant Pat. No. 5,454), and an unnamed nectarine seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Kay Diamond". The present variety was hybridized in 1986 by us in a cultivated area of our experimental orchard at Bradford Farms near Le Grand, Calif. in Merced County (San Joaquin Valley). It was the result of a seedling using May Diamond Nectarine (U.S. Plant Pat. No. 5,454) as the selected seed parent and an unnamed nectarine seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety is similar to that of the Spring Bright Nectarine (U.S. Plant Pat. No. 7,507) by producing fruit that matures in mid June, that is almost full red in skin color, that is very firm in texture, and that is flavorful in taste, but is distinguished therefrom and an improvement thereon by being higher in chilling requirements, by having a small blossom instead of large, and by producing fruit that is freestone instead of clingstone.

The present variety is similar to its selected seed parent, the May Diamond (U.S. Plant Pat. No. 5,454), in fruit appearance by being a full red colored freestone nectarine with excellent firmness, but is distinguished therefrom and an improvement thereon by producing fruit that ripens 12 days later, is larger in size, and is sweeter in flavor.

DRAWING

The accompanying photograph exhibits four whole fruits positioned to display the characteristics of the skin color and form, one fruit divided around the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Jun. 22, 1993. All major color code designations are by reference to the Inter-Society Color Council, National Bureau of Standards. Common color names are also used occasionally.

TREE

Size: Large.
Vigor: Vigorous.
Growth: Upright and dense.
Form: Vase formed.
Hardiness: Hardy.
Production: Very productive.
Bearing: Regular bearer.
Trunk:
- *Size.*—Medium.
- *Texture.*—Shaggy.
- *Bark Color.*—Brownish gray [64. brGy].
- *Lenticels.*—Numerous. Color: Deep yellowish brown [75. deep yBr]. Size: Typically ⅛" to ⅜", [3.2–9.5 mm.].

Branches:
- *Size.*—Medium.
- *Texture.*—Medium.
- *Color.*—1st year wood topside: Dark pink [6. d.Pk]. 1st year wood underside: Brilliant yellow green [116. brill.YG]. Older wood: Grayish brown [61. gy.Br].
- *Lenticels.*—Medium, small.

Leaves:
- *Size.*—Medium. Average length: 5⅝" [142.9 mm.]. Average width: 1 5/16" [33.3 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125. m.OlG]. Ventral surface: Moderate yellow green [120. m.YG].
- *Margin.*—Finely serrate.
- *Venation.*—Pinnately net veined.

*Petiole.*—Average length: 7/16" [11.1 mm.]. Average thickness: 1/16" [1.6 mm.]. Color: Light yellow green [119. l.YG].

*Stipules.*—Numerous. Average length: ¼" [6.4 mm.].

*Glands.*—Numbers: Mostly 4 to 6 per leaf. Position: Mostly alternately positioned on base of blade. Size: Small. Form: Reniform. Color: Light greenish yellow [101. l.gY].

Flower buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Small.

*Color.*—Moderate pink [5. m.Pk].

FRUIT

Maturity when described: Hard but eating ripe.

Date of first picking: Jun. 16, 1993.

Date of last picking: Jun. 28, 1993.

Size: Uniform, large.

*Average diameter axially.*—2¾" [69.9 mm.].

*Average traversely in suture plane.*—2½" [63.5 mm.].

Form: Uniform, symmetrical, globose.

*Longitudinal section form.*—Round to oval.

*Transverse section through diameter.*—Round.

Suture: An inconspicuous shallow line extending from the base to slightly beyond the apex, with slight depression beyond the pistil point.

Ventral surface: Rounded, lipped slightly throughout.

Lips: Slightly unequal.

Cavity: Flaring, circular suture plane with suture showing on one side.

*Depth.*—5/16" [7.9 mm.].

*Breadth.*—⅝" [15.9 mm.].

Base: Slightly truncate.

Apex: Rounded.

Pistil point: Negligible in length, mostly depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—Virtually none observed.

*Color.*—Very dark red [17.v.d.R] to moderate red [15. m.R] with moderate orange yellow [71. m.OY] freckling toward the apex.

Flesh:

*Color.*—Light yellow [86. l.Y] to the pit with some slight moderate red [15. m.R] flecking with increasing maturity.

*Surface of pit cavity.*—Covered with light yellow [86. l.Y] fibers.

*Amygdalin.*—Scarce.

*Juice.*—Abundant, rich.

*Texture.*—Very firm, crisp.

*Fibers.*—Abundant, fine, tender.

*Ripens.*—Evenly.

*Flavor.*—Acidic and sweet.

*Aroma.*—Slight.

*Eating quality.*—Very good.

STONE

Type: Freestone, but tight with virtually no air spaces.

Form: Elliptical.

Base: Straight.

Apex: Acute to acuminate.

Sides: Equal.

Surface: Irregularly furrowed toward the apex and pitted toward the the base.

Ridges: Jagged toward the base.

Color: Moderate yellowish brown [77. m.yBr].

Pit wall: ¼" [6.4 mm.] thick.

Tendency to split: Slight in wet season.

Kernel:

*Form.*—Oval.

*Taste.*—Sweet.

*Viable.*—Yes.

*Average width.*—½" [12.7 mm.].

*Average length.*—¾" *to* 13/16" [19.1–20.6 mm.].

*Color.*—Pale yellow [89. p.Y].

*Pellicle color.*—Light grayish yellowish brown [79. l.gy.yBr].

*Amygdalin.*—Scant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is similar to the Spring Bright Nectarine (U.S. Plant Pat. No. 7,507) by producing fruit that matures in mid June, that is full red in skin color, that is very firm in texture, and that is flavorful in taste, but is distinguished therefrom and an improvement thereon by by having reniform instead of globose glands, by having a higher chilling requirement, by having a small blossom instead of large, and by producing fruit that is freestone instead of clingstone.

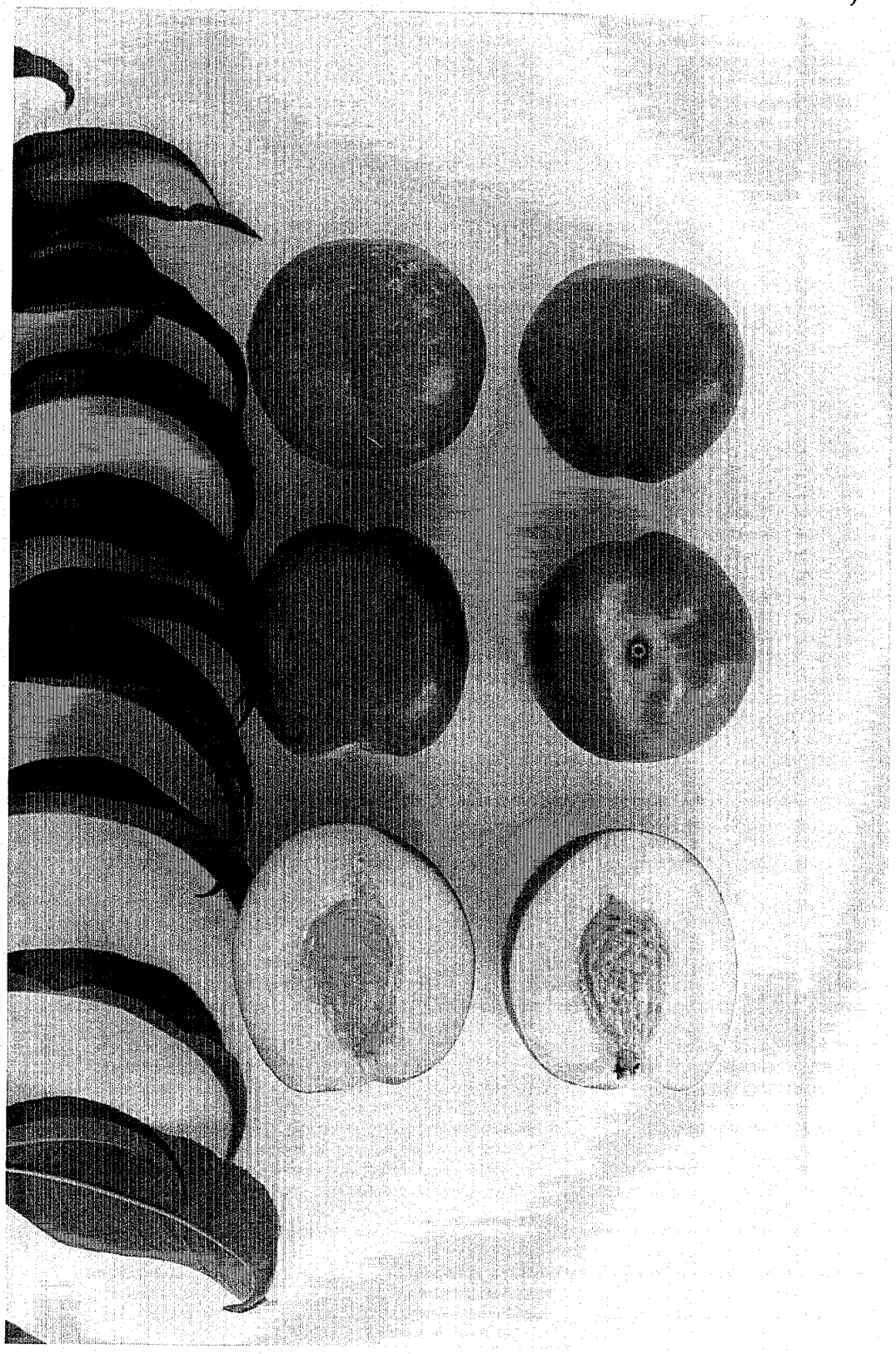

* * * * *